United States Patent [19]
Hammerman

[11] Patent Number: 5,976,524
[45] Date of Patent: Nov. 2, 1999

[54] CHIMERIC KIDNEY

[75] Inventor: Marc Hammerman, St. Louis, Mo.

[73] Assignee: Washington University, St. Louis, Mo.

[21] Appl. No.: 08/797,201

[22] Filed: Feb. 11, 1997

Related U.S. Application Data

[63] Continuation of application No. 08/779,159, Jan. 6, 1997, abandoned.

[51] Int. Cl.$^6$ .............................. A61K 48/00; A01N 1/02
[52] U.S. Cl. .......................................... 424/93.1; 435/375
[58] Field of Search ............................... 424/93.1, 93.21, 424/9.2, 9.1; 435/375

[56] References Cited

U.S. PATENT DOCUMENTS

| | | | |
|---|---|---|---|
| 5,759,830 | 6/1998 | Vacanti et al. | 435/180 |
| 5,770,417 | 6/1998 | Vacanti et al. | 435/180 |

OTHER PUBLICATIONS

Woolf, MD, A.S., et al., "Integration of New Embryonic Neprons Into the Kidney", *Amer. Jour. of Kidney Diseases*, vol. XVII, 6:611–614 (Jun. 1991).

Woolf, A.S., et al., "Creation of a functioning chimeric mammalian kidney", *Kidney Intl. . .* , vol. 38:991–997 (1990).

Churchill, M., "Kidney Transplants in Cyclsporine–Treated Sprague–Dawley Rats", *Transplantation*, vol. 49, No. 1:8–13 (Jan. 1990).

Bobert, B., "Evidence that embryonic kidney cells expressing flk–1 are intrinsic, vasculogenic angioblasts", *Amer. Physiol. Soc.*, pp. F744–753 (1996).

Abrahamson, D.R., et al., "Glomerular Development in Intraocular and Intrarenal Grafts of Fetal Kidneys", *Lab. Investigation*, vol. 64, No.5:629–639 (1991).

Barakat, T.I., et al., "The capacity of fetal and neonatal renal tissues to regenerate and differentiate in a heterotopic allogeneic subcutaneous tissue site in the rat", *J. Anat.*, 110; 3:393–407 (1971).

Cooper, D.K.C., et al., "The Pig as Potential Organ Donor for Man", Springer–Verlag; Nonimmunological Considerations; pp. 481–500 (1991).

Simpson, M., "Immunosuppression in xenotransplantation", *Xenograft 25*; pp. 273–284 (1989).

Somerville, C.A., et al., "Future directions in transplanation: Xenotransplantation", *Kidney Intl. . .* , vol. 44; Suppl. 42:S–112—S–121 (1993).

Rogers, S.A., et al., "Insulin–like Growth Factors I and II are Produced in the Metanephros and are Required for Growth and Development In Vitro", *The Jour. of Cell Biol.*, vol. 113, No. 6:1147–1453 (Jun. 1991).

Armstrong et al., "Embryonic kidney rudiments grown in adult mice fail to mimic the Wilms' pheynotype, but show strain specific morphogenesis," *Experimental Nephrology*, vol. 1(3): 168–174, May 1993.

Tisinai et al., "Comparison of growth, neovasculation and enzymatic function of fetal intestinal grafts in the omentum and renal capsule," *J. of Pediatric Surgery*, vol. 25 (8): 914–916, Aug. 1990.

Koseki et al., "Integration of embryonic nephrogenic cells carrying a reporter gene into functioning nephrons," *American J. of Physiology*, vol. 261(3.1): C550–C554, Sep. 1991.

Woolf et al. "Origin of glomerular capillaries: Is the verdict in?" *Experimental Nephrology*, vol. 6(1): 17–21, 1998.

*Primary Examiner*—Brian R. Stanton
*Assistant Examiner*—Karen M. Hauda
*Attorney, Agent, or Firm*—Richard F. Trecartin; Flehr Hohbach Test; Albritton & Herbert LLP

[57] ABSTRACT

Methods for increasing the nephron mass of a mammalian recipient are disclosed. A metanephros from an allogenic or xenogeneic mammalian donor is implanted next to a recipient's omentum or under the renal capsule of the recipient's kidney. The metanephros becomes vascularized by the recipient's blood vessels, forming a chimeric kidney that produces urine and develops a ureter that facilitates externalization of the urine. A ureter to ureter anastomosis can be subsequently performed to provide fluid communication between the chimeric kidney ureter and a ureter of the recipient.

16 Claims, 2 Drawing Sheets

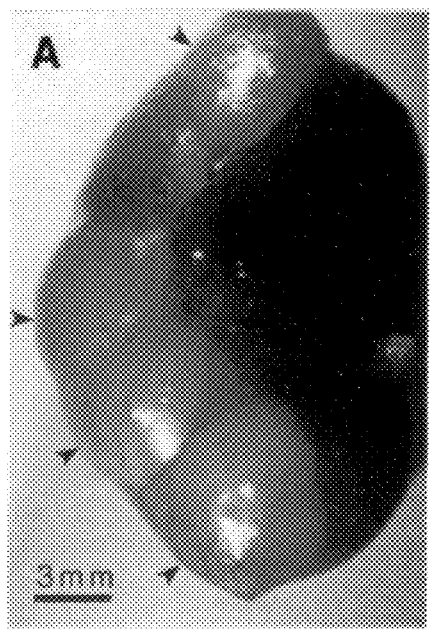
FIG._1A
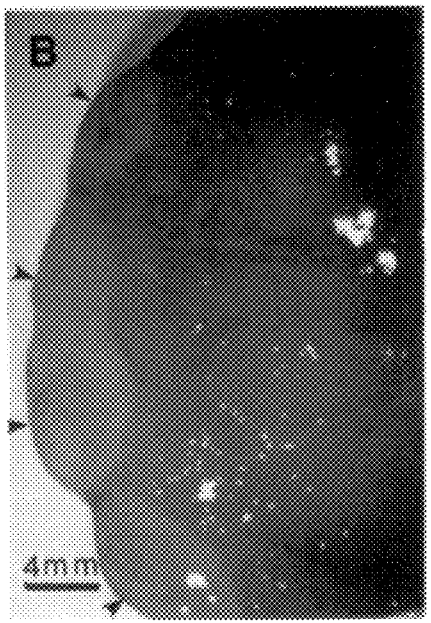
FIG._1B

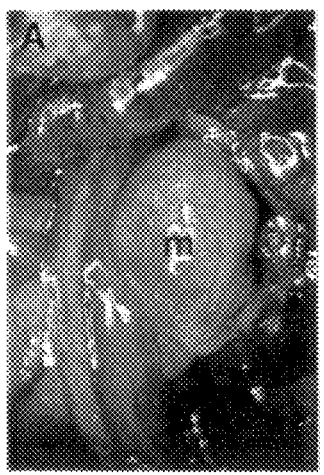
FIG._2A
FIG._2B
FIG._2C

CHIMERIC KIDNEY

RELATED APPLICATION

This application is a continuation of U.S. Ser. No. 08/779,159, filed Jan. 6, 1997, now abandoned.

This invention was made with Government support from the National Institute of Health Grant/Contract No. P50 DK45181. The Government may have certain rights to this invention.

BACKGROUND OF THE INVENTION

Kidneys are excretory organs that serve the general function of maintaining the chemical and physical constancy of blood and other body fluids. They remove superfluous water and biologically useless as well as toxic materials that accumulate in the blood.

In vertebrates, the kidneys are paired, bean-shaped organs, with each kidney having a convex lateral or external border, and a medial, internal border which is concave in the center and convex toward either extremity. The central part of the medial border has a deep fissure called the hilum, through which extends vessels, nerves and the ureter. The hilum expands into a central cavity called the renal sinus. Each kidney is surrounded by a smooth, fibrous capsule and is comprised of an internal medullary surrounded by an external cortical substance. The medullary substance consists of striated conical masses termed renal pyramids, arranged such that their bases are directed toward the lateral border, while their apices converge toward the renal sinus. The cortical substance lies immediately beneath the fibrous capsule and arches over bases of the pyramids and extends between adjacent pyramids towards the renal sinus.

Microscopically, the kidney is comprised of a number of functional units called nephrons. The human kidney is comprised of about 1.25 million nephrons. Each nephron has a complex structure with two main parts: the glomerulus and the renal tubule. The glomerulus is a tuft of nonanastomosing capillaries located in the cortical substance which is derived from an arteriole called the afferent vessel which branches to form the capillary loops. The capillaries join to form the efferent arteriole The glomerulus is surrounded by a double-walled membranous sac called the capsule of Bowman, which is part of the renal tube. The renal tubule is located partly in the cortical substance, where it pursues a convoluted, circuitous course and forms the capsule of Bowman, and partly in the medullary substance, in which the convolutions of the tubule disappear. As it enters the medullary substance, it becomes straight, and dips down for a variable depth, then bends to form the loop of Henle and ascends back into the cortical substance where it again becomes tortuous and terminates into a collecting tubule which opens into a ureter. The ureter opens into the urinary bladder.

During embryogenesis, the rudiments of the permanent kidneys, the metanephros, make their appearance during the fifth week of gestation in humans, during day 12 of embryonic rat development and during day 11 of embryonic mouse development. At this stage of development, outgrowths of the mesonephric ducts, called ureteric buds, collect about their distal ends, intermediate mesoderm caudal to the mesonephros, designated metanephric blastema. Numerous outgrowths arise from the distal end of the ureteric bud which push radially into the surrounding mass of metanephric blastema and give rise to the collecting ducts of the kidneys. The proximal ends of the ureteric bud give rise to the ureter and renal pelvis. The metanephric blastema differentiates into all of the tubular structures of the adult renal tubule with the exception of the collecting system. Nephron segment growth and differentiation that occurs in metanephric organ culture recapitulates closely that which occurs in vivo. One exception is that vascularization of the nephron does not take place in the metanephric organ culture system because the origin of the glomerular blood vessels is, in part, extrametanephric. Humans develop a full complement of nephrons by approximately 35 weeks of gestation. However, in rodents nephrogenesis is not complete at the time of birth, but rather continues for the first 3 weeks following birth, when nephrons continue to develop from a nephrogenic zone located at the periphery of the kidney.

Once renal development is complete, no new nephrons are formed under any conditions. Renal arteries deliver blood to the glomerulus, where blood plasma is filtered through the porous walls of the capillaries. The filtrate drains into the tube system where the major part of water and plasma components are reabsorbed into the blood vessels. The remaining liquid containing biologically useless materials in a high concentration is the urine that passes through the ureter to the urinary bladder. Urine contains hundreds of organic compounds, including the protein digestion and metabolism products, urea, creatinine, uric acid and others. The loss of functional renal mass that occurs following insults to the adult kidney, is compensated for in the short term, by hypertrophy and hyperfunction of the remaining nephrons. However, these compensatory changes are often transient and under some circumstances maladaptive in that they may lead to further loss of functional renal mass. When kidneys cannot operate properly, useless and/or toxic materials accumulate in blood and other physiological fluids and can lead to illness and death.

End-stage chronic renal failure in humans afflicts more than 250,000 individuals in the United States, most of whom are treated using dialysis. External hemodialysis removes excess water and biologically useless organic compounds from the patient. A drawback of this treatment results from the unselectivity of the diffusion process through the polymeric membrane that is used, which does not distinguish between useless molecules and useful molecules, such as amino acids, nucleotides, mineral ions and many other useful components. Additionally, the treatment is generally unpleasant for the patient because before dialysis, the waste products build up in the body, and after dialysis there is an imbalance of chemical equilibria and processes in the body due to removal of essential components. Thus, considerable morbidity is associated with dialysis treatment. Additionally, hemodialysis is an expensive, time-consuming process, which keeps the patient connected to the dialysis machine for several hours, three or four times a week.

Another method of treating kidney failure is to replace the malfunctioning kidneys with a functioning kidney from a donor organism. In the United States approximately 5,000 kidneys transplantations are performed annually. Because the kidneys are paired organs, and only one is necessary for normal life, live volunteer donors, in addition to cadaveric donors, can be used to provide the donor kidney. The drawbacks associated with transplantation are the availability of donor kidneys and immunological rejection by the transplant recipient of the donor organ.

Attempts have been made to increase renal mass by allogeneic kidney grafting. Woolf et al. transplanted pieces of metanephric tissue from embryonic mice into tunnels made into the renal cortex of recipient neonatal mice (less than one day old) which were still undergoing nephrogenesis [*Kidney International*, Vol. 38 (1990), ¶. 991–997; and American J. of Kidney Diseases, Vol. XVII, No. 6 (June 1991) ¶. 611–614]. Two to four weeks later, the chimeric kidneys were removed from the mice. The donor tissue was observed to contain mature, functioning, differentiated features within the nephrons which indicated that post-transplantation differentiation occurred within the donor metanephric tissue. When adult mice were grafted with pieces of metanephric tissue, using the same procedure that was used for the neonatal mice, the donor tissue was extruded from the cortex and resembled a poorly-differentiated tumor underneath the renal capsule. The investigators concluded that the neonatal kidney, which in mice still undergoes nephrogenesis after birth, can facilitate differentiation of an embryonic implant, but that this ability is lacking in the fully-differentiated adult kidney.

Barakat and Harrison, J. Anat. (1971), Vol.110, 3, ¶. 393–407, sectioned metanephroi originating from embryonic rats (days 15–17) and kidneys from newborn rats (<1 day), into quarters, and transplanted each quarter into a subcutaneous site in the abdominal wall of either a newborn or adult rat. Within the newborn hosts, the grafts formed fully differentiated glomeruli and tubules by 8 days post-transplantation. However, with the adult hosts, there was significant lymphocytic infiltration into the grafts after the same amount of time. By 11 to 12 days, the grafts within the adult hosts were largely replaced by fibrosis. Irrespective of whether the grafted renal tissue was of fetal or neonatal origin, each of the adult host rats rejected its graft.

Abrahamson et al. transplanted whole embryonic (day 17) rat kidneys under the renal capsule of mature rat hosts [Laboratory Investigation, Vol. 64, No. 5, ¶. 629–639 (1991)]. Considerable glomerulogenesis and tubulogenesis occurred, although structural abnormalities were present. While, the implanted kidneys had become connected to the host vasculature, no observations were made as to whether functioning nephrons were present.

Signs of rejection were apparent in all of the grafts within 10 days post-transplantation.

Immunosuppression treatments have been used to prevent rejection of allografts. Churchill et al. performed experiments where the left kidneys of adult rats were removed and replaced by donor adult rat kidneys [Transplantation, Vol. 49: 8–13 (1990)]. Non-immunosuppressed recipients rejected the transplanted kidneys, while rejection was prevented in recipients immunosuppressed with daily injections of Cyclosporine A.

SUMMARY OF THE INVENTION

A method of increasing the nephron mass of a recipient in need thereof is described. The method comprises implanting metanephric tissue obtained from an embryonic donor at an appropriate stage of fetal development under the renal capsule of the kidney of the recipient, or into an omental fold of the recipient under conditions that allow the metanephric tissue to become vascularized by the recipient's blood vessels and develop to form mature, functioning nephrons within the recipient. The embryonic donor can be allogeneic or xenogeneic to the recipient.

Brief Description of the Drawings

FIG. 1A is a photograph of a chimeric kidney removed four weeks post-transplantation from a rat recipient. Four cysts under the capsule of the kidney are shown (arrowheads).

FIG. 1B is a photograph of a parasagittal section of a chimeric kidney, removed four weeks post-transplantation, that shows structures resembling small kidneys (arrowheads) approximately 7 mm in diameter embedded into a recipient kidney.

FIG. 2A is a photograph of a metanephros (m), in situ, six weeks after transplantation into an omental fold of an adult rat.

FIG. 2B is a photograph of a metanephros (m) which was removed from an omental fold of a recipient adult rat six weeks after transplantation. Also shown is one of the recipient's kidneys (k) which has a diameter approximately three times that of the metanephros.

FIG. 2C is a photograph of a metanephros (m), with intact ureter (u), removed six weeks after transplantation into an omental fold of a recipient adult rat.

DETAILED DESCRIPTION OF THE INVENTION

This invention relates to increasing the nephron mass of an animal by implanting metanephric tissue, obtained from an embryonic donor at an appropriate stage of fetal development, either underneath the renal capsule of the recipient's kidney or into an omental fold of the recipient. The recipient can be a juvenile, or an adult, and can be allogeneic or xenogeneic to the donor. The implanted metanephric tissue becomes vascularized by the recipient's vasculature, and differentiates to form functioning nephrons, as evidenced by the formation of urine, which may be contained in cysts, within the donor tissue.

The donor metanephric kidney is harvested at the appropriate stage of fetal development, which is preferably soon after the metanephric kidney begins formation and prior to the development of blood vessels within the metanephros originating from inside or outside the metanephros. If the embryonic renal tissue is harvested prior to this time, it will differentiate into non-renal tissues such as hair and gut once implanted into the recipient tissue. However, tissue harvested too late in the development of the metanephric kidney that contains blood vessels, may contain more antigen-presenting cells and cell-surface antigens and thus present more of threat of rejection by the recipient. Thus, there is a "window of opportunity" during which the transplantation of metanephroi into a recipient results in the development of viable chimeric kidneys.

The appropriate developmental stage for harvesting the metanephros will vary depending upon the species of donor. Generally, the metanephros can be harvested 1 to 5 days after the metanephros forms. Preferably, the metanephros is harvested from 1 to 4 days after the metanephros forms, and more preferably from about 2 to 4 days after metanephros formation. In rats, the metanephros forms on day 12.5 of a 22-day gestation period, and on day 11 of a 19 day gestation period in mice. In these species, a suitable time frame in which to harvest the donor metanephros of mice or rats is between the second and fourth day after the metanephros begins formation. Preferably the metanephros is harvested within 3 days after formation of the metanephros begins.

In species having a longer gestation period, the time-frame during which the metanephros is suitably harvested following its formation, may be longer. Generally, the time frame in which the metanephros is harvested will be less than about one fifth of the total gestation period of the donor, preferably less than about one seventh of the total gestation period of the donor, and more preferably, less than about one tenth of the total gestation period of the donor. Table 1 shows the time-course (in days) of metanephros development and gestational period in some vertebrates.

TABLE 1

|  | Metanephros Formation (days) | Gestational Period (days) |
|---|---|---|
| Human | 35–37 | 267 |
| Macaque | 38–39 | 167 |
| Pig | 20–30 | 114 |
| Guinea Pig | 23 | 67 |
| Rabbit | 14 | 32 |
| Rat | 12.5 | 22 |
| Mouse | 11 | 19 |
| Hamster | 10 | 16 |
| Chick | 6 | 21 |

Pigs are preferred xenogeneic donors for humans because of their comparable organ size, and availability. Pig metanephroi are harvested at about the 10 mm stage. This occurs between approximately embryonic day 20 and embryonic day 30. Human tissue could be used as an allogeneic source for transplantation.

Metanephroi are removed surgically under a dissecting scope and suspended in suitable medium, such as a 1:1 mixture of Dulbecco's modified Eagles Medium and Hams F12 medium (Rogers et al. *J. Cell Biol.* 113:1447–1453 (1991), and placed on ice under sterile conditions, until they are transplanted. They should be transplanted as soon as possible into the recipient, preferably within one hour after removal from the embryonic donor, and more preferably, within 30 minutes. It is preferred to leave the whole metanephros intact for transplantation. One or more metanephroi may be used per recipient, depending upon the increase in nephron mass that the recipient needs.

Surgery is performed on the recipient to expose one or both kidneys. The donor metanephroi can be implanted directly into the recipient's kidney to result in the formation of chimeric kidney, or into a fold of the omentum where it forms a chimeric kidney that functions independently of the recipient's kidney. The omentum, which is a membranous structure the connects the bowels, is a preferred site for the implant. While a donor metanephros can be placed adjacent to any portion of the omentum, it is preferable to implant it in an omental fold which will retain the developing kidney at the site of implantation. It is most preferable to implant the metanephros at an omental fold located near one of the recipient's kidneys, particularly near the ureter, so that the developing ureter of the metanephros can be readily connected to the recipient's excretory system.

When implanted into the recipient's kidney, an incision, large enough to receive the donor tissue is made in the fibrous renal capsule that surrounds the recipient kidney. The location of the incision can be anywhere in a viable portion of the recipient kidney, but most conveniently will be at an external border of the kidney that is easily accessible during surgery. The donor tissue is placed between the capsule and the cortex of the recipient kidney.

The implanted metanephroi are allowed to grow and differentiate within the recipient under conditions that allow the metanephric tissue to vascularize and develop to form mature, functioning nephrons. Suitable conditions may include the use of pre or post-operative procedures to prevent rejection of the implant. In some cases of allogeneic transplantation, there may be no host rejection of the transplanted metanephros. However, in the case of xenogeneic transplantation, rejection prevention measures must be taken. Typically, this will be done by immunosuppressing the recipient after the transplantation. Cyclosporine A (CSA) treatments can provide sufficient immunosuppression to prevent rejection of the donor tissue. CSA treatment regimens to prevent transplant rejection are known in the medical field. Local immunosuppression techniques are described by Gruber, *Transplantation* 54:1–11 (1992), incorporated by reference. In U.S. Pat. No. 5,560,911, antibodies directed against idiotypes on naturally occurring human anti-animal antibodies are disclosed for use in inhibiting xenograft rejection. The anti-idiotypic antibodies are injected into the xenograft recipient in order to bind to the idiotypes expressed on anti-xenograft antibodies. Anti-idiotypic antibodies that bind human anti-pig antibodies, to prevent rejection of transplanted pig tissues by a human patient are exemplified. Anti-lymphocyte globulins are also known for prevention of transplant rejection (Lacy et al. *Diabetes*, Vol. 30: 285–291 (1981)). As an alternative to immunosuppression, the implanted metanephros can be treated prior to transplantation to reduce its antigenicity. Exemplary approaches to the reduction of immunogenicity of transplants by surface modification are disclosed by Faustman WO 92/04033 (1992).

Metanephric kidneys transplanted using the techniques described herein grow, and become vascularized in large part by the recipient to form chimeric kidneys. It is believed that the vascularization by the recipient may facilitate the acceptance of transplanted xenogeneic tissue. When implanted into the recipient's kidney, the metanephroi become imbedded into the parenchyma of the recipient kidney. The donor metanephroi begin to form various mature structures that are distinguishable from the structures in the adjacent recipient renal tissue, including mature glomeruli and tubules, renal papilla, and ureter.

After a sufficient period of development, it is evident that the glomeruli are capable of filtering plasma. Hence, implantation of the metanephric tissue contributes to an increase in the nephron mass of the recipient.

Filtering glomeruli are evidenced by the detection of urine within the donor metanephroi. This can be done by measuring the levels of urea nitrogen and/or creatinine in fluid aspirated from the donor tissue. Such fluid may be contained within one or more cysts associated with the donor tissue (see Example 1). Urine is defined herein as fluid having a concentration of creatinine and/or urea nitrogen that is higher than the concentration of the corresponding components found in the recipient's plasma. The concentration differential varies, and will be reduced with increased hydration of the recipient. However, generally, the concentration of creatinine in the donor metanephroi will be at least twice the concentration found in the recipient's plasma. The concentration of urea nitrogen in the donor metanephroi will generally be at least fifty percent greater than the concentration of urea nitrogen in the recipient's plasma.

In order to facilitate the externalization of the urine that forms within the donor renal tissue of chimeric kidneys, standard ureter to ureter anastomosis procedure can be used to hook up the ureter from donor kidneys with that of the recipient kidney. When the metanephroi are implanted into the omentum of the recipient, externalization of urine can be achieved by linking the ureter directly to the recipient's ureter or bladder. These procedures, and other procedures known in the art for the externalization of urine are summarized in *Adult and Pediatric Urology*, 3rd Ed., Gillenwater, et al., Eds. ¶. 987–994 and 2369–2375 (1996). In some cases, post-transplantation surgery may be unnecessary as the intrarenal transplanted donor kidneys may incorporate into the collecting system of the host.

In order that the invention described herein may be more fully understood, the following examples and are set forth.

It should be understood that these examples are for illustrative purposes only and are not to be construed as limiting the scope of the invention in any manner.

EXAMPLE 1

Allogeneic Transplantation of Metanephroi into Host Kidney

Transplantation Methods

Whole metanephroi, with renal capsules intact, were removed surgically under a dissecting scope from E15 Sprague-Dawley rat embryos (Harlan, Indianapolis Ind.), and suspended in saline solution on ice under sterile conditions. Within 45 minutes after removal, four metanephroi per recipient were implanted under the capsule of normal kidneys of 6 week old outbred normal (NL) female Sprague-Dawley rats. Some of the recipient rats had undergone contralateral nephrectomy (UNX) or unilateral nephrectomy and one-half contralateral kidney infarction (1½ NX) using the procedures described in S. A. Rogers et al., *J. cell. Biol.*, 113:1447 (1991). Transplanted metanephroi were approximately 700 um in diameter and, as would be expected for this stage of development, contained segments of ureteric bud and some developing nephrons, but no glomeruli. When noted, recipient rats received Cyclosporine A (CSA) beginning post-transplantation (5 mg/kg body weight per day injected subcutaneously) in vehicle (peanut oil). As a control, vehicle only was injected.

Structural Development of Metanephroi

Four or six weeks later, kidneys were removed from the rats. When recipient kidneys were examined post-transplantation, cysts containing clear fluid surrounded the sites where metanephroi were transplanted under the capsule of NL, UNX or 1½ NX rats. Four cysts under the capsule of a kidney from a vehicle-treated NL rat 4 weeks post-transplant are shown in FIG. 1A arrowheads). Structures resembling small kidneys approximately 7 mm 7000 um) in diameter were present under the cysts and were embedded into he larger recipient kidney. Thus, the diameter of the transplanted metanephroi had increased 10-fold reflecting a 1000-fold increase in volume.

Four such structures embedded into the parenchyma of a kidney from a vehicle treated 1½ NX rat four weeks post-transplantation are shown in FIG. 1B (arrowheads). Histological examination of fixed, paraffin-embedded, and sliced sections of the tissue mass stained with hematoxylin and eosin revealed that the structures were integrated into the parenchyma of recipient kidneys, and that clusters of lymphocytes were present at the transplant-recipient interface.

Metanephroi transplanted into kidneys of vehicle-treated rats that had undergone 1½ NX underwent growth, development and vascularization in vivo. They contained mature glomeruli and tubules that could be distinguished from glomeruli and tubules in adjacent recipient renal tissue by their smaller size and different staining characteristics in paraffin sections stained with hematoxylin and eosin. Blood vessels were present in transplanted metanephroi. Some were identifiable as arteries. Glomeruli in transplanted metanephroi contained red blood cells, distinguishing them from glomeruli of rat metanephroi grown in organ culture, in which vascularization does not occur. Cysts were present within the parenchyma of transplanted metanephroi that contained structures resembling a renal papilla. Other structures were lined with transitional epithelium characteristic of the ureter. Lymphocytes accumulated around the periphery of transplanted metanephroi, but there was no evidence of rejection of tubular or vascular elements. Similar growth, development and vascularization of metanephroi transplanted into rats that had undergone UNX or into kidneys of NL rats were observed.

Metanephroi transplanted into kidneys of CSA-treated 1½ NX rats were examined 4 weeks post-transplantation. Results of such transplantations were similar to those into kidneys of vehicle-treated 1½ NX rats except no peripheral lymphocytes were observed.

Integration of Transplanted Metanephroi into Recipient Renal Tissue

To determine whether transplanted metanephroi became integrated into recipient kidneys, kidneys of NL rats 6 week post-transplantation were examined. To clear blood from the organ, kidneys were perfused using a modified Ringers solution injected into the aorta distal to the renal arteries following occlusion of the aorta proximal to the kidneys and transection of the inferior vena cava. This results a blanching of the kidney as blood is replaced by perfusate. Normally, the entire kidney blanches as described by Bortz et al. [*J. Cell Biol.*, 107:811 (1988)]. However, following perfusion of kidneys that contained a transplanted metanephros, blood remained in the transplanted structure relative to the recipient kidney. Most likely, this reflects a reduced perfusion in chimeric blood vessels (derived from transplant and host kidneys) that have been shown to supply transplanted metanephroi relative to perfusion in those supplying the host kidney (Robert et al., *Am. J. Physiol.*, 271:F744 (1996)). Blood could be traced into the papilla of the recipient kidney in a distribution characteristic of the vasa recta as described by Dworkin et al. (*The Kidney*, B. M. Brenner ed. W. B. Saunders Philadelphia, å. 247–260 (1996)).

Kidneys were stained using tetragonobolus purpurea lectin (TPL), as described by Rogers et al., *Am. J. Physiol.* 264:F996 (1993), which is expressed in collecting ducts of developing rat kidneys prior to birth and for several weeks following birth, but not in collecting ducts of kidney from adult rats. In adult rat kidney, TPL is expressed in distal tubules and medullary thick ascending limbs of Henle's loop. In recipient kidney tissue, TPL was expressed in cortex within distal tubule and medullary thick ascending limb as would be expected. However, TPL was also expressed in a population of collecting ducts which radiate from the transplanted metanephros into the papilla of the recipient kidney together with blood-containing vasa recta which would be expected to provide their blood supply, evidencing that the collecting system and vasa recta of the transplanted metanephros become incorporated into the papilla of the recipient kidney.

Testing of Chimeric Kidney Function

Levels of urea nitrogen and creatinine were measured in aspirated cyst fluid, and in blood from the aorta, and urine from the bladder of the 1½ NX vehicle-treated rats using methods described by Rogers et al. [(*Am. J. Physiol.* 264:F917 (1993)]. Levels of urea nitrogen were increased 2.6-fold and 15-fold, respectively, in cyst fluid and bladder urine relative to blood, and levels of creatinine were increased 12-fold and 28-fold, respectively, as shown in Table 2 (All measurements were made at the time of sacrifice; comparisons were made using the multiple comparison procedure described by C. W. Dunnett, *J. Am. Statistical Assoc.* 50:1096 (1955)). Thus, both urea nitrogen and creatinine were concentrated in cyst fluid relative to blood, indicating that the cyst fluid was urine. The concentrations of urea nitrogen and creatinine in the cyst fluid were significantly less than the concentrations in bladder urine, indicating that the cyst urine did not originate from leaked bladder urine. This is consistent with reports that the ability of a 4 week-old kidney (transplanted kidney) to clear the blood of urea nitrogen and creatinine relative to a 10 week-old kidney (recipient kidney), is reduced [Aperia et al., Am. J. Physiol., 228:1319 (1975)].

TABLE 2

| Plasma Creatinine/ureaN* | Cyst Fluid Creatinine/ureaN* 1½ NX rats (n = 7) | Bladder Urine Creatinine/ureaN* |
|---|---|---|
| 1.14 ± .08/53.8 ± 6.3 | 13.4 ± 2.2/136 ± 16 | 32.3 ± 5/800 ± 72 |

Creatinine
Plasma < cyst fluid, p < 0.01
Cyst fluid < bladder urine, p < 0.01
UreaN (urea nitrogen)
Plasma < cyst fluid, p < 0.01
Cyst fluid < bladder urine, p < 0.01
*mg/dl

EXAMPLE 2

Xenogeneic transplantation of metanephroi into host kidney

Metanephroi from N.I.H. Swiss mouse metanephroi (E14) were transplanted underneath the renal capsule of 1½ NX Sprague Dawley rats. Four weeks post-transplantation, all that remained of the metanephroi implanted into the kidneys of rats that did not receive CSA treatment was a mass of fibrotic tissue. However, in CSA-treated recipients, metanephroi grew, vascularized and developed. The presence of a urothelial-lined cavity containing a renal papilla in the transplanted metanephroi indicated that glomerular filtration occurs in the donor renal tissue.

EXAMPLE 3

Allogeneic transplantation of metanephroi into host omentum

Metanephroi were dissected from E15 sprague-Dawley rats as previously described in Example 1 and implanted into 6 week old outbred UNX Sprague Dawley rats in omental folds near the recipients' kidneys. Recipient rats received no immunosuppression post-transplantation.

After 6 weeks, the transplanted metanephroi were removed and examined. They had assumed a kidney-like shape in situ, had intact ureters and were approximately one-third the diameter of native kidneys. Sections of transplanted metanephroi were prepared and staeosin. Both cortical and meeosin. Both cortical and medullary tissue were present. Cortices contained well-developed glomeruli containing red blood cells, proximal tubules with well-developed brush border membranes, and distal tubules. Medullas contained well-developed collecting ducts. Ureters were lined with transitional epithelium. Rare accumulations of lymphocytes were observed, but there was no evidence of rejection of tubular or vascular elements.

All cited references are incorporated herein by reference in their entirety.

What is claimed is:

1. A method of increasing the nephron mass of a mammalian recipient comprising implanting at least one whole metanephros of an embryonic mammalian donor next to the recipient's omentum or under the renal capsule of the recipient's kidney under conditions that allow the metanephros to become vascularized, forming a chimeric kidney that produces urine and develops a ureter that facilitates externalization of the urine.

2. The method of claim 1 wherein the metanephros is implanted next to the recipient's omentum.

3. The method of claim 2 wherein the metanephros is implanted into an omental fold near the recipient's kidney.

4. The method of claim 1 wherein the metanephros is implanted under the renal capsule of the recipient's kidney.

5. The method of claim 1 wherein the metanephros has an intact renal capsule.

6. The method of claim 1 wherein at least two whole metanephroi with renal capsules intact are implanted into the recipient.

7. The method of claim 1 wherein the metanephros is allogeneic to the recipient.

8. The method of claim 1 wherein the embryonic donor is xenogeneic to the recipient.

9. The method of claim 8 further comprising immunosuppressing the recipient.

10. The method of claim 1 wherein the metanephros is obtained from the donor within 2 to 4 days after embryonic development of the metanephros begins.

11. The method of claim 1 wherein the metanephric tissue is obtained from the donor prior to the presence of blood vessels within the metanephric tissue.

12. The method of claim 1 wherein the recipient has reduced functional renal mass prior to implantation of the metanephros.

13. The method of claim 1 wherein after the chimeric kidney ureter develops, a ureter to ureter anastomosis is performed to provide fluid communication between the chimeric kidney ureter and a ureter of the recipient.

14. The method of claim 1 wherein the mammalian recipient is a juvenile or adult.

15. The method of claim 1 wherein the metanephros is implanted within one hour after removal from the embryonic donor.

16. The method of claim 1 wherein prior to implantation of the metanephros, renal tissue is removed from the mammalian recipient.

* * * * *